(12) United States Patent
Cailler et al.

(10) Patent No.: US 9,821,079 B2
(45) Date of Patent: Nov. 21, 2017

(54) FLUORESCENT CONJUGATES

(71) Applicant: SURGIMAB S.A.S., Montpellier (FR)

(72) Inventors: Françoise Cailler, Montpellier (FR); Bérénice Framery, Juvignac (FR)

(73) Assignee: SURGIMAB S.A.S., Montpellier (FR)

( * ) Notice: Subject to any disclaimer, the term of this patent is extended or adjusted under 35 U.S.C. 154(b) by 0 days.

(21) Appl. No.: 15/297,975

(22) Filed: Oct. 19, 2016

(65) Prior Publication Data
US 2017/0035915 A1 Feb. 9, 2017

Related U.S. Application Data

(63) Continuation of application No. PCT/EP2016/062557, filed on Jun. 2, 2016.

(30) Foreign Application Priority Data

Jun. 3, 2015 (EP) .................................... 15170617

(51) Int. Cl.
| | | |
|---|---|---|
| *A61B 10/00* | (2006.01) | |
| *A61B 5/00* | (2006.01) | |
| *A61B 8/00* | (2006.01) | |
| *A61K 49/00* | (2006.01) | |
| *A61K 39/395* | (2006.01) | |
| *C07K 16/30* | (2006.01) | |
| *C07K 16/28* | (2006.01) | |
| *G01N 33/574* | (2006.01) | |

(52) U.S. Cl.
CPC .... *A61K 49/0058* (2013.01); *A61K 39/39525* (2013.01); *A61K 49/006* (2013.01); *A61K 49/0032* (2013.01); *C07K 16/28* (2013.01); *C07K 16/3007* (2013.01); *G01N 33/57492* (2013.01); *C07K 2317/24* (2013.01)

(58) Field of Classification Search
CPC .. A61K 49/00; A61K 49/0058; A61K 49/006; A61K 49/0032; A61K 39/39525; C07D 207/30; C07K 16/28; C07K 2317/24; C07K 16/3007; G01N 33/57492
USPC ............. 424/1.11, 1.49, 1.65, 1.69, 9.1, 9.6; 514/1, 1.1; 548/560
See application file for complete search history.

(56) References Cited

U.S. PATENT DOCUMENTS

2008/0318336 A1  12/2008  Scherninski et al.

FOREIGN PATENT DOCUMENTS

| WO | WO 2000/016810 | 3/2000 |
| WO | WO 2001/043781 | 6/2001 |
| WO | WO 2012/027623 | 3/2012 |

OTHER PUBLICATIONS

Folli et al., "Immunophotodiagnosis of Colon Carcinomas in Patients Injected With Fluoresceinated Chimeric Antibodies Against Carcinoembryonic Antigen", Proc. Natl. Acad. Sci., vol. 89, p. 7973-7977, (1992).
Gutowski et al., "Intraoperative Immunophotodetection for Radical Resection of Cancers: Evaluation in an Experimental Model", Clinical Cancer Research, vol. 7, p. 1142-1148, (2001).
International Search Report of International Application No. PCT/EP2016/062557, dated Aug. 16, 2016, 6 pages.
Pauli et al., "An in Vitro Characterization Study of New Near Infrared Dyes for Molecular Imaging", European Journal of Medicinal Chemistry, vol. 44, p. 3496-3503, (2009).
Xiao et al., "Heptamethine Cyanine Based 64Cu-PET Probe PC-1001 for Cancer Imaging: Synthesis and In Vivo Evaluation", Nucl Med Biol., vol. 40(3), p. 351-360, (2013).

*Primary Examiner* — D L Jones
(74) *Attorney, Agent, or Firm* — Hoxie & Associates LLC

(57) ABSTRACT

The invention provides a conjugate with fluorochrome moiety F coupled to a targeting moiety T. Moiety F is described by formula (I), and the targeting moiety T is characterized in that it has affinity to a tumor marker, such as an antibody or antibody fragment. The conjugate may be used for tumor diagnostics including photodetection of tumor nodules during resection surgery.

14 Claims, 3 Drawing Sheets

FLUORESCENT CONJUGATES

CROSS REFERENCE TO RELATED APPLICATIONS

This application is a continuation application under 35 U.S.C. §111 (a) of International Application Serial No. PCT/EP2016/062557, filed Jun. 2, 2016, which claims the benefit of European Application No. 15170617.3, filed on Jun. 3, 2015, the contents of each of which are incorporated herein by reference in their entireties.

FIELD

The present invention is in the field of biomedical research and relates in particular to compounds and methods useful in diagnostics, for example in the in vitro or in vivo diagnosis of tumours.

BACKGROUND

Cancer currently accounts for approx. 13% of all deaths worldwide. In spite of decades of intense research, cancer remains the second leading cause of death in the highly developed countries, accounting for approx. 25% of the deaths. For many types of cancer, surgery—often in combination with chemotherapy, radiation treatment or hyperthermia—is the mainstay of therapeutic intervention.

A cancer is also referred to as a malignant neoplasm, or a malignant tumour. A neoplasm is an abnormal growth of tissue. Neoplasms are differentiated into benign neoplams, precancerous or in situ neoplasms, and malignant neoplasms. Many but not all neoplasms also form tumours, which are solid or fluid-filled lesions that can be differentiated anatomically from the unaffected tissue. Like neoplasms, tumours may be benign, precancerous, or malignant. In common language as well as in the description of the present invention, however, the term "tumour" may be used synonymously with "malignant tumour".

The vital prognosis of cancer patients depends upon the stage of the disease when it is first diagnosed. Twenty to thirty percent of the patients suffering from gastrointestinal cancers will develop locoregional recurrence as a unique relapse. Epithelial ovarian tumours also display locoregional evolution when they reach stage III. It was demonstrated several years ago that complete surgical resection is a very important factor for the improvement of the prognosis of the patients. This maximal cytoreduction strategy is part of therapeutic protocols that include systemic or intraperitoneal chemotherapy possibly associated with hyperthermia.

The setup of a curative surgery is a major parameter for the future of the patients. Detection of the totality of tumour nodules and their disseminations is a major point influencing post-surgery prognosis. Differentiation between tumour and normal tissues is not always easy, especially when patients have been given neo-adjuvant treatments. Surgeons are then only guided by their visual and tactile senses, and by their experience; there is no intra-operative technique available at the moment to help them visualise the extensions of the tumour.

It has been suggested that cancer resection surgery may be improved by the use of in situ photodetection. Photodetection relies on the exposure of the potentially affected tissues with a compound having affinity to a tumour and being able to be optically visualised at a selected wave length of light.

Photodetection of tumours was originally developed in the 1980s with the use of hematoporphyrin derivates such as photofrin. The major limitations of photodiagnosis with these molecules are their low selectivity for cancerous tissues and their capacity to react chemically and induce high photosensitization or necrosis. This latter limitation is, in fact, an advantage in photodynamic therapy, for which these compounds were also proposed.

Folli et al. used a conjugate of an antibody against the carcinoembryonic (CEA) antigen with fluorescein to visualise tumours in patients with colorectal carcinoma (Proc. Natl. Acad. Sci. USA, vol. 89, pp. 7973-7977, 1992). Immunophotodetection of lesions of colon carcinoma LS174T with a conjugate of the anti-CEA MAb 35A7 and indocyanine (Cy5) was demonstrated in a mouse model by Gutowsky et al. (Clin. Cancer Res., vol. 7, pp. 1142-1148, 2001).

However, the clinical utility of these conjugates is rather limited. Conjugates of antibodies with fluorescein possess a rather low excitation and emission wavelength, resulting in low tissue penetration and a substantial degree of nonspecific autofluorescence of the non-cancerous tissues induced by the laser light used for exciting the dye component. The toxicology of Cy5 conjugates is unknown and not yet well-established in the literature.

The present invention addresses these and other associated problems and drawbacks of tumour photodetection. One of the objects of the invention is to provide improved conjugates useful for photodetection of malignant or precancerous tumours which are clinically viable, which overcome one or more drawbacks of the prior art, and which have one or more of the following properties: A high degree of tumour specificity, a high sensitivity such as to allow the detection of very small tumour lesions, good clinical tolerability, high stability, little interference with other dyes, and good manufacturability.

A further object of the invention is to provide improved diagnostic methods for tumours, both in vitro and in vivo, using such conjugates. Used in vivo, such diagnostic methods may be part of novel treatments, such as improved tumour resection methods.

A further object of the invention is to provide methods for preparing such conjugates.

Further objects of the invention will be clear on the basis of the following description of the invention and the patent claims.

SUMMARY OF THE INVENTION

In brief, the invention provides a fluorescent conjugate comprising a fluorochrome moiety F coupled to a targeting moiety T, wherein moiety F has the formula (I) as defined herein-below, wherein Y is for each occurrence independently selected from $SO_3H$, $SO_3-$ and $SO_3M$; M is a monovalent cation; x, z and y are independently selected from an integer of 1 to 8; and wherein moiety T has affinity to a tumour marker. In one embodiment, the fluorochrome moiety F may have the formula (II) as defined below.

The tumour marker to which the targeting moiety T has affinity may be a tumour antigen, such as an antigen expressed or overexpressed by certain tumour cells. An example of such antigen is carcinoembryonic antigen (CEA). The targeting moiety T itself may be a non-peptidic ligand, an antibody, an antibody fragment, or a fusion protein comprising at least one variable region of an antibody. In one embodiment, the targeting moiety T is an antibody, in particular a chimeric, humanised or human monoclonal antibody.

In a further aspect, the invention provides a composition comprising such conjugate, optionally in combination with further active or inactive ingredients. For example, the composition may be sterile and comprise inactive ingredients such as water for injection, buffer components, one or more stabilisers such as amino acids, lyophilisation aids such as mono-, di- or oligosaccharides, isotonising agents and the like. The composition may also comprise a small amount of the targeting moiety T in unconjugated form.

In a yet further aspect, the invention provides a method for preparing the conjugate. The method comprises the steps of (a) providing a fluorochrome having the formula (III) as defined below, wherein Y is for each occurrence is independently selected from $SO_3H$, $SO_3$— and $SO_3M$; wherein M is a monovalent cation, x, z and y are independently selected from an integer of 1 to 8, and Z is selected from a counterion, hydrogen, succinimidyl, sulfosuccinimidyl, and nitrophenyl; (b) providing a targeting agent having affinity to a tumour marker; and (c) coupling the fluorochrome with the targeting agent. In one embodiment, the fluorochrome has the formula (IV) as defined below.

Furthermore, the invention provides clinical and non-clinical uses of the conjugate and of the composition comprising the conjugate. The in vitro use includes the use for detecting a tumour cell or tumour cells in a sample, or for diagnosing and/or monitoring a tumour in vitro. Clinically, the conjugate and/or the composition comprising the conjugate may be used for detecting foci of a tumour that expresses the tumour marker or for determining the location of a tumour that expresses the tumour marker in a patient. For example, they may be used for detecting tumour cells or tumour tissue at a resection margin in a patient undergoing, or having undergone, resection surgery. In one embodiment, a composition comprising the conjugate is administered to a patient having a tumour that expresses the tumour marker to which the targeting moiety T has affinity, e.g. by intravenous, intraperitoneal, subcutaneous, or intramuscular injection or perfusion or by inhalation or by topical administration, for example as a spray; commencing tumour resection surgery on the patient within not more than about 72 hours thereafter, and illuminating a tissue at a resection site of the patient undergoing the resection surgery with light having a wavelength of about 660 to 700 nm. In this way, the localisation of the tumour—including the localisation of very small nodules or lesions which are otherwise invisible to the naked human eye—will be visualised such as to guide the surgeon to resect the tumour tissue completely and/or to verify the completeness of the resection.

DETAILED DESCRIPTION OF THE INVENTION

Figure 1:
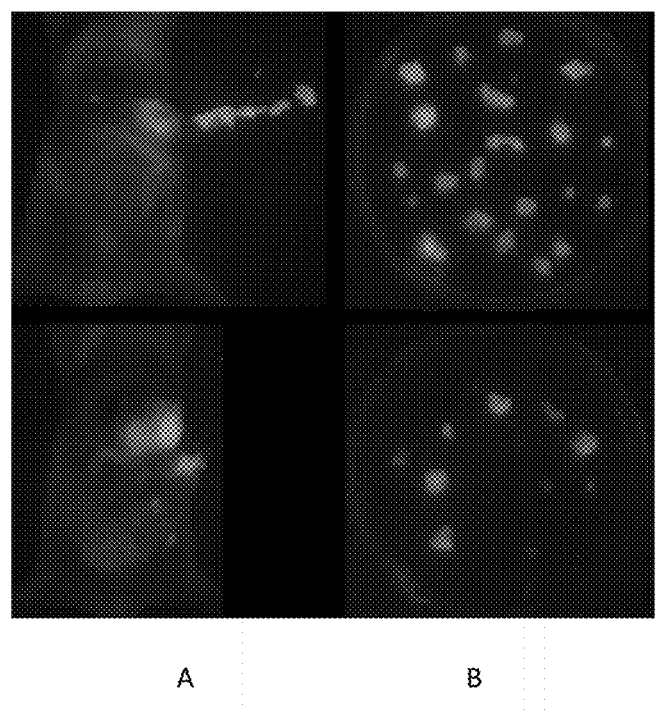
FIG. 1 depicts fluorescence of tumoral micronodules in situ (column A) and resected (column B) in a LS-174T peritoneal carcinomatosis mouse model, visualized at 700 nm after administration of 20 μg of the fluorescent conjugate of Ex. 3.

In a first aspect, the present invention provides a fluorescent conjugate comprising a fluorochrome moiety F coupled to a targeting moiety T, wherein moiety F has the formula (I):

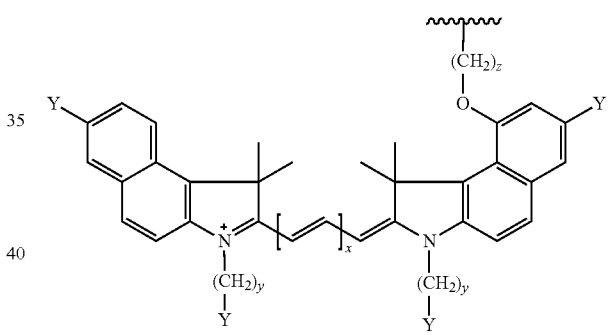

wherein Y is selected independently for each occurrence from $SO_3H$, $SO_3$— and $SO_3M$; M is a monovalent cation; x, z and y are independently selected from an integer of 1 to 8; and wherein moiety T has affinity to a tumour marker.

Examples for monovalent cations include, without limitation, Na, K, or ammonium. In one of the preferred embodiments, Y is selected from $SO_3$— and $SO_3Na$.

The fluorochrome moiety F, which may also be referred to as a fluorescent dye or label, or a fluorophore moiety, of the fluorescent conjugate of the invention absorbs electromagnetic energy at a wavelength range preferably in the ultraviolet, visible spectrum or infrared and emits at a generally longer wavelength range, preferably in the visible or near-infrared range. As understood herein, the term excitation wavelength (expressed in nm) refers to the peak, i.e. maximal or specific absorption wavelength of the fluorochrome, or that of the fluorescent conjugate comprising the fluorochrome moiety coupled to a targeting moiety T. The term emission wavelength (expressed in nm) refers to the peak, i.e. maximal or specific emission wavelength of the fluorochrome or that of the fluorescent conjugate comprising the fluorochrome moiety coupled to a targeting moiety of the invention.

The fluorochrome moiety F is a cyanine derivative of Formula (I) as described above and preferably emits in the far visible or near-infrared (NIR) spectrum with a peak emission wavelength range of between 650 and 750 nm. When coupled to the targeting moiety T, the resulting conjugate also preferably emits in a peak emission range of between 650 and 750 nm.

It has been found by the inventors that these fluorochrome moieties have particularly favourable fluorescent characteristics such as quenching, quantum yield, and in particular robustness towards photobleaching, enabling them to be reliably used in conjugation with targeting moieties which active towards antigens.

With respect to Y, the skilled person will appreciate that, depending on the chemical environment of the conjugate, the $SO_3H$, $SO_3$—, $SO_3M$ and/or $SO_3Na$ groups may also be dynamically converted into each other. For example, when dissolved in an aqueous medium, and depending on the pH and the availability of other cations, a group represented by Y and selected from $SO_3$—, $SO_3M$ and/or $SO_3Na$ may also become protonated into $SO_3H$, or it may be converted into another salt form such as from $SO_3Na$ to $SO_3K$ or vice versa. Accordingly, the present invention covers such alternative forms of the compound of formula (I).

Particularly preferred conjugates are those comprising a fluorochrome moiety F of Formula (II):

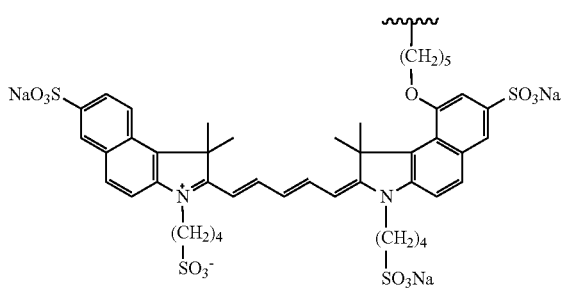

In the fluorescent conjugates, the fluorochrome moiety F is coupled to a targeting moiety T; preferably it is covalently linked i.e. conjugated to the targeting moiety T by means of a covalent bond such as an amide or ester bond.

As mentioned in the context of formula (I), formula (II) should also be interpreted with respect to the groups represented by Y such as to include alternative sulfonic acid forms such as $SO_3H$ or $SO_3K$ that are generated in situ under chemical equilibrium, depending on e.g. the composition and/or the pH value of an aqueous medium in which the conjugate may be dissolved. Moreover, it should be understood that each of the four sulfonic acid groups in Formula (II) may be in the form of the Na salt or inner salt and that Formula (II) as depicted represents just one of the various possibilities of representing the compound.

The targeting moieties T of the fluorescent conjugates have affinity towards tumour markers and can bind or associate with a tumour marker. A tumour marker is to be understood as a product or molecule produced by or present in a tumour, or produced by a patient's normal cellular mechanisms in response to the presence of a tumour. As used herein, unless a different meaning is obvious from the particular context, a tumour means a neoplasm, which is a group or mass of cells or tissue arising from abnormal or uncontrolled cell growth. In particular, the tumour marker is produced by a tumour which is cancerous or malignant.

The tumour marker may be, for example, in the form of a protein, a glycoprotein, a receptor, a hormone, an enzyme, an antigen, or an oncogene or a product thereof. The tumour marker may be over-expressed by the tumour cells in comparison to normal cells, or it may be a tumour-specific substance that is uniquely produced by the tumour cells. Particularly preferred tumour markers towards which the targeting moiety T may be targeted or directed are those that are cell-surface proteins or receptors which are presented on the tumour cell surface and/or those which are in particularly expressed in epithelial cells or in solid tumours such as carcinomas or sarcomas.

In a preferred embodiment of the invention, the tumour marker is a tumour antigen. A tumour antigen is a molecule or product that is specific to, or associated with, tumour cells (for example over-expressed in tumour cells), which can induce or stimulate an immune system reaction such as the production of antibodies and T cells and/or B-cell response. The tumour antigen may represent or comprise a protein or a lipid. It may be glycosylated (e.g. a glycoprotein), and may possess one or more epitopes, i.e. regions or domains to which an antibody, B cell or T-cell may preferably bind or have a particular affinity.

Exemplary tumour antigens include tumour antigens derived or generated from oncoviral proteins, oncofetal antigens which are normally produced at higher levels only during fetal development, antigens that are overexpressed or accumulated by the tumour cell relative to a normal cell, or antigens which are mutants or post-translationally-altered. Preferably the tumour marker is a tumour antigen selected from carcinoembryonic antigen (CEA), epidermal growth factor receptor (EGFR) and human epidermal growth factor receptor-2 (HER2).

In a preferred embodiment of the invention, the tumour antigen is carcinoembryonic antigen (CEA). CEA is an oncofetal glycoprotein with a molecular weight of 180-200 kDa that is expressed in epithelial cells. CEA is expressed at high levels on the cell surface particularly in malignant tumours of the colon and rectum (overexpressed in 95% of colorectal cancers), as well as malignant tumours of the stomach, small intestine, pancreas, liver, breast, ovary, cervix, bladder, gall bladder and lung. CEA is typically not localized and may be expressed over the entire cell surface as well as intraglandular lumina and intracellular lumina. The CEA antigen comprises five major epitopes classified as GOLD-1 to GOLD-5, as defined in Hammarström et al. (Cancer Res 1989 (49) 4852-4858), to which an anti-CEA antibody or antibody fragment or fusion protein may have binding specificity.

In one of the preferred embodiments, the targeting moiety T of the fluorescent conjugate of the invention targets and binds to a CEA antigen-expressing tumour which may be located in one or more tissues or organs of a patient selected from the colon, the rectum, stomach, small intestine, pancreas, liver, breast, ovary, cervix, bladder, gall bladder, lung and oesophagus.

In another preferred embodiment, the targeting moiety T of the fluorescent conjugate may bind to a tumour marker which is a receptor. The receptor may be tumour cell specific or may be over-expressed and present at higher levels in tumour cells. The targeting moiety T may act as a ligand in respect of such receptors, and may be a small non-peptidic molecule, i.e. a chemical entity or compound which does not incorporate or comprise of any amino acids sequences.

In a preferred embodiment, the fluorescent conjugate of the invention comprises a fluorochrome of formula (I) or (II) and a targeting moiety T selected from a non-peptidic ligand, an antibody, an antibody fragment, and a fusion protein comprising at least one variable region of an antibody. Preferably, any one such targeting moiety is capable of binding specifically to a tumour antigen such as CEA, HER2, or EGFR. In one specific embodiment, the fluorescent conjugate comprises a fluorochrome of formula (I) or (II) and a targeting moiety T selected from a non-peptidic ligand, an antibody, an antibody fragment, and a fusion protein comprising at least one variable region of an antibody, which targeting moiety binds specifically to CEA.

In one particular embodiment, the targeting moiety T is an antibody or an antibody fragment, or a fusion protein comprising at least one variable region of an antibody. In this case, the antibody, antibody fragment or the at least one variable region of an antibody of a fusion protein may be derived from, or belong to any of the IgG, IgA, IgD, or IgM immunoglobulin isotypes or classes. A full length antibody is typically a Y-shaped glycoprotein comprising an Fc (fragment crystallisable) domain and a Fab (fragment antigen binding) domain. These are constructed from a pair of heavy chain (H) and light chain (L) polypeptide structures interlinked via disulfide bonds to form the Y-shaped structure. Each chain comprises a variable region (V) and a constant region (C). The heavy chain comprises a variable chain region ($V_H$) and various constant regions (abbreviated $C_H1$, $C_H2$ etc.); whereas the light chain only comprises a variable chain region ($V_L$) and a constant region ($C_L$). The variable regions are involved with the recognition and binding specificity of the antibody to a particular epitope of the antigen, and form the antigen-binding Fab domains.

Antibody fragments refer to any region, chain, or domain of an antibody, or any construct, stabilized form or conjugate thereof which is capable of interacting and binding specifically to an antigen. Exemplary antibody fragments include fragment antigen-binding domains (Fab, or Fab'), Fab constructs, single-chain variable fragments (scFv), single domain antibodies such as VHH, minibodies, diabodies etc. Fusion protein refers to a construct comprising of an antibody fragment fused to another bioactive protein or polypeptide.

In a preferred embodiment, the targeting moiety T of the fluorescent conjugate of the invention is a monoclonal antibody (mAb). This may be produced via methods known in the art. Chimeric monoclonal antibodies are particularly preferred. These are hybrid monoclonal antibodies comprising domains or regions of heavy or light chains derived from more than one species, such as from human and murine antibodies. Optionally, the targeting moiety T of the fluorescent conjugate may be a humanized antibody (generally comprising predominantly of at least 85-95% human-derived sequences) or a human antibody derived solely from human germline antibody sequence.

Preferably, any one such targeting moiety T is capable of binding specifically to the tumour antigen CEA.

In one embodiment, the targeting moiety T of the fluorescent conjugate comprising a fluorochrome moiety F of formula (I) is a chimeric monoclonal antibody with binding specificities to one or more of the epitopes of the CEA antigen, for example the GOLD-1, GOLD-2, GOLD-3, GOLD-4, or GOLD-5 epitopes. In one specific embodiment, the targeting moiety T has affinity to, and/or specificity for, the GOLD-2 epitope. In a further embodiment, the fluorochrome moiety F of such conjugates is of formula (II) as described above.

In a particularly preferred embodiment, the invention provides a fluorescent conjugate comprising a fluorochrome moiety F coupled to a targeting moiety T, wherein moiety F has the formula (II), and wherein moiety T is a chimeric mAb directed against the GOLD-2 epitope of CEA, comprising heavy chains of the G1m3 allotype and light chains of the km3 allotype, each heavy chain and each light chain comprising at least one mouse IgG1 variable domain and at least one human constant domain. This chimeric monoclonal antibody has binding specificity, as determined by competitive binding/inhibition tests known in the art, to the GOLD-2 epitope of CEA.

In particular, the fluorescent conjugate may be coupled to a chimeric mAb directed against CEA expressed and prepared from the following nucleotide sequences:

```
(A) Heavy Chain (SEQ ID NO: 1):
GGTACCGCCGCCACCATGGACTCCAGACTGAACCTGGTGTTCCTGGTGCT

GATCCTGAAGGGCGTGCAGTGCGACGTGCAGCTGGTGGAATCTGGCGGAG

GACTGGTGCAGCCTGGCGGCTCCAGAAAGCTGTCTTGTGCCGCCTCCGGC

TTCACCTTCTCCAACTTCGGCATGCACTGGATCCGGCAGGCCCCTGAGAA

GGGCCTGGAATGGGTGGCCTATATCTCCGGCGGCTCCTCCACCATCTACT

TCGCCGACACCCTGAAGGGACGGTTCACCATCTCCCGGGACAACCCCAAG

AACACCCTGTTTCTGCAGATGACCTCCCTGCGGAGCGAGGACACCGCCAT

CTACTACTGCGCCAGAGACTACTACATCAACAACTACTGGTACTTCGACG

TGTGGGGCGCTGGCACCACCGTGACAGTGTCATCTGCTAGC (B) Light Chain (SEQ ID NO: 2):
GTCGACGCCGCCACCATGGAATTTCAGACCCAGGTGTTCGTGTTCGTGCT

GCTGTGGCTGTCTGGCGTGGACGGCGACATCGTGATGACCCAGTCCCAGA

AATTCATGTCCACCTCCGTGGGCGACCGGGTGTCCATCACATGCAAGGCC

TCTCAGAACGTGCGGAGCGCCGTGGCCTGGTATCAGCAGACACCTGGCCA

GAGCCCCAAGGCCCTGATCTACCTGGCCTCCAACAGATACACCGGCGTGC

CCGATCGGTTCACCGGCTCTGGCTCTGGCACCGACTTCACCCTGACCATC

TCCAACGTGCAGTCCGAGGACCTGGCCGACTACTTCTGTCTGCAACACTG

GAACTACCCCCTGACCTTCGGCGGAGGCACCAAGCTGGAACTGAAGCGTA

CG
```

The variable heavy chain nucleotide sequence (A) above includes at the 5' and 3' ends respectively, sequences for KpnI and NheI restriction sites. The variable light chain nucleotide sequence (B) includes respectively at the 5' and 3' end of the sequence, SalI and BSiWI restriction site sequences.

The amino acid sequence of the variable regions of this mAb corresponds to the following sequence:

```
(A) Heavy Chain (SEQ ID NO: 3):
Asp Val Gln Leu Val Glu Ser Gly Gly Gly Leu Val Gln Pro Gly Gly Ser Arg Lys Leu Ser Cys Ala Ala Ser Gly Phe Thr Phe Ser Asn Phe Gly Met His Trp Ile Arg Gln Ala Pro Glu Lys Gly Leu Glu Trp Val Ala Tyr Ile Ser Gly Gly Ser Ser Thr Ile Tyr Phe Ala Asp Thr Leu Lys Gly Arg Phe Thr Ile Ser Arg Asp Asn Pro Lys Asn Thr Leu Phe Leu Gln Met Thr
```

-continued

```
Ser Leu Arg Ser Glu Asp Thr Ala Ile Tyr Tyr Cys

Ala Arg Asp Tyr Tyr Ile Asn Asn Tyr Trp Tyr Phe

Asp Val Trp Gly Ala Gly Thr Thr Val Thr Val Ser

Ser (B) Light Chain (SEQ ID NO: 4):
Asp Ile Val Met Thr Gln Ser Gln Lys Phe Met Ser Thr Ser Val Gly Asp Arg Val Ser Ile Thr Cys Lys Ala Ser Gln Asn Val Arg Ser Ala Val Ala Trp Tyr Gln Gln Thr Pro Gly Gln Ser Pro Lys Ala Leu Ile Tyr Leu Ala Ser Asn Arg Tyr Thr Gly Val Pro Asp Arg Phe Thr Gly Ser Gly Ser Gly Thr Asp Phe Thr Leu Thr Ile Ser Asn Val Gln Ser Glu Asp Leu Ala Asp Tyr Phe Cys Leu Gln His Trp Asn Tyr Pro Leu Thr Phe Gly Gly Gly Thr Lys Leu Glu Leu Lys
```

In a preferred embodiment of the invention, the fluorescent conjugate may comprise a moiety F having the formula (II) coupled to a targeting moiety T, wherein T is a chimeric mAb directed against CEA comprising a variable light chain region of SEQ ID NO: 4 and a variable heavy chain of SEQ ID NO: 3.

The fluorescent conjugate of the invention may comprise more than one fluorescent moiety F conjugated to one targeting moiety T, such as from 1 to about 10 moieties F per targeting moiety T. Preferably, the number of fluorochrome moieties F coupled to one targeting moiety T is selected from 1 to 4. In other words, in a molecule of such preferred conjugate, n moieties F are coupled to one moiety T, and n is an integer selected from 1 to 4.

While an individual conjugate molecule is characterised by n being an integer, the compound comprising a plurality of conjugate molecules may have a degree of conjugation, or average number of moieties F per moiety T, which does not have to be an integer, but which is preferably any value in the range from about 1 to about 4.

In this context, the targeting moiety T is preferably selected from an antibody, an antibody fragment, and a fusion protein comprising at least one variable region of an antibody, and one to four fluorochrome moieties F of formula (I) conjugated to it. In one embodiment of the invention, the targeting moiety T is an anti-CEA chimeric monoclonal antibody coupled to n fluorochrome moiety F of formula (II), wherein n is in the range from 1 to 4.

A further aspect of the invention covers a composition comprising the fluorescent conjugate as described above.

In one embodiment, the composition comprises a mixture of different fluorescent conjugates which differ solely or primarily in their degree of conjugation. In another specific embodiment, the composition comprises a mixture of at least 3 or 4 conjugates, all of which comprise a fluorochrome moiety F having formula (II) coupled to a chimeric mAb having affinity to the GOLD-2 epitope of CEA, and wherein the at least 3 or 4 conjugates differ from each other in that the number of fluorochrome moieties F coupled to one targeting moiety T is 1, 2, and 3, respectively; or 1, 2, 3, and 4, respectively.

The composition may further comprise a compound representing the targeting moiety T in unconjugated form (or theoretically, a conjugate with a degree of substitution of zero). For example, in combination with the previously described embodiment, such composition comprises the unconjugated chimeric mAb having affinity to the GOLD-2 epitope of CEA along with the at least three or four conjugates of the same mAb coupled with 1, 2, 3, and optionally 4 or more fluorochrome moieties F according to formula (II), respectively. The conjugate populations of this mixture can be determined by methods known in the art, for example via mass spectrometry (e.g. MALDI-TOF).

The average degree of conjugation of the conjugates in the composition is preferably from about 0.5 to about 3. The degree of conjugation is the fluorochrome to antibody molar ratio which can be determined spectrophotometrically. Thus the figure should be understood to reflect the average degree of conjugation of the conjugates and any unconjugated antibody present in the composition. In another embodiment, the average degree of substitution is from about 1 to about 2. The inventors have found that while a higher degree of substitution may provide improved visualization, the affinity towards the tumour marker of the targeting moiety decreases with an increased number of fluorochrome moieties conjugated to it. It was determined that a degree of substitution from about 0.5 to about 3, in particular for compositions comprising conjugates of a chimeric mAb having affinity to the GOLD-2 epitope of CEA with a fluorochrome according to formula (II) works best in that it allows for excellent visualisation of even small nodules of a tumour expressing CEA during surgery.

The composition of the invention may further comprise excipients such as buffers, stabilizers, cryoprotectants, and isotonic agents, pH adjustment agents. Particularly preferred excipients are basic amino acids such as L-arginine and salts thereof, salts such as citrate, sodium or potassium phosphate salts, sodium chloride, potassium chloride, saccharides such as trehalose, mannitol, maltose, sucrose, or dextran, or a nonionic surfactant such as a polysorbate or a poloxamer. The pH of the composition is preferably between 5.2 and 7.2. Preferably, the composition is prepared under sterile conditions known in the art and is sterile.

In a particular embodiment, the composition comprising any of the above defined fluorescent conjugates is sterile and further comprises an aqueous buffer and L-arginine. and/or comprises a compound comprising moiety T which is not coupled to moiety F. In a further embodiment, the composition comprising any of the above defined fluorescent conjugates is sterile and comprises an aqueous buffer adjusted to a pH of about 6.0, L-arginine hydrochloride, and a polysorbate, preferably polysorbate 20. A saccharide such as trehalose, mannitol, maltose or sucrose may also optionally be included in these compositions.

In another particular embodiment, the concentration of the fluorescent conjugate in the composition, based on the content of the targeting moiety, for example the anti-CEA mAb (as determined by spectrophotometry or HPLC methods known in the art) is between 1 mg/mL and 10 mg/mL.

A yet further aspect of the invention provides for a method for the preparation of a fluorescent conjugate, comprising the steps of (a) providing a fluorochrome having the formula (III):

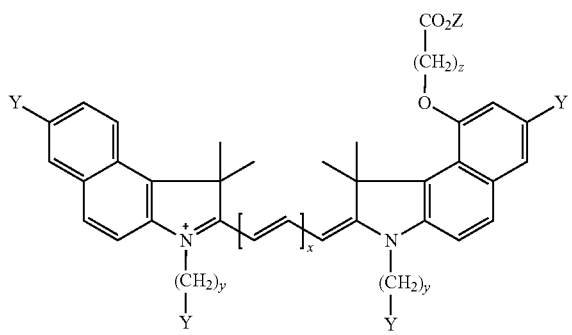

wherein Y is independently for each occurrence selected from $SO_3H$, $SO_3-$ and $SO_3M$, wherein M is a monovalent cation; x, z and y are independently selected from an integer of 1 to 8, and Z is selected from a counterion, hydrogen, succinimidyl, sulfosuccinimidyl, and nitrophenyl; (b) providing a targeting agent having affinity to a tumour marker; and (c) coupling the fluorochrome with the targeting agent.

Examples for monovalent cations include, without limitation, Na, K, or ammonium. In one of the preferred embodiments, Y is selected from $SO_3-$ and $SO_3Na$.

The fluorescent conjugates of the invention comprising a fluorochrome moiety F coupled to a targeting moiety T, wherein moiety F has the formula (I) and wherein the targeting moiety T has affinity to a tumour marker may be obtainable by such methods of preparation.

The same options and preferences regarding the targeting moiety T and the fluorochrome moiety F as described in the context of the conjugate itself in any of the preceding paragraphs also apply to the targeting agent and the fluorochrome to be used in the method. Accordingly, the targeting agent is preferably a compound comprising the targeting moiety T of the conjugate, and the fluorochrome used in the method is preferably a compound comprising, or yielding, the fluorochrome moiety F of the conjugate. The targeting agent preferably has affinity to a tumour antigen, such as the carcinoembryonic antigen (CEA). The affinity to CEA may be to any one of its known epitopes such as the GOLD-2 epitope. In a particularly preferred embodiment, the targeting agent is a chimeric monoclonal antibody having affinity to CEA.

The chimeric monoclonal antibody (mAb) having affinity to CEA may be produced by means of expression from CHO cells which have been transfected with an expression vector encoding the chimeric mAb. Preferably, the expression vector comprises nucleotide sequences encoding for antibody human constant domains and anti-CEA antibody murine variable domains, preferably variable domains with the sequence as described above.

The fluorochromes useful for preparing the conjugates may be prepared in analogy to the reaction scheme of Diagram Ia and methods described in U.S. Pat. No. 8,034, 626. For example, the fluorochromes may be synthesised from the condensation of two indolenine derivatives comprising the requisite sulfonate and (alkyl)oxy substitutions, wherein one of the indolenine derivatives is in the form of an acetanilodo derivative. In one embodiment, an indolenine intermediate may be prepared from an amino-aromatic precursor, via the steps of diazotation/reduction followed by the steps of sulfonation, hydroxylation, Fischer cyclization with a ketone to the indolenine, carboxylyalkylation of the hydroxyl substituent and quarternization with a sultone.

In another embodiment, the fluorochrome is a compound of formula (IV):

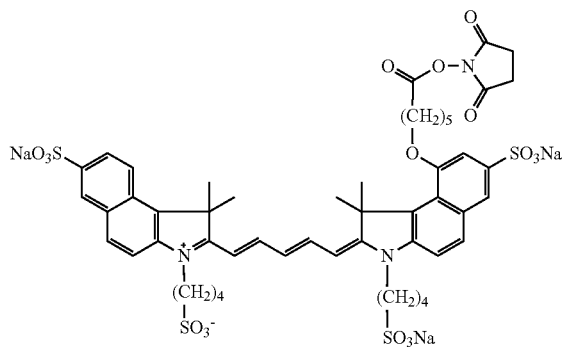

The fluorochromes of the invention may be activated, preferably as an active ester (e.g. succinimidyl ester) for conjugation with a targeting moiety T. In one embodiment, the fluorochrome of formula (I) or (II) is coupled to the targeting moiety T by means of amide, ester, thioester, disulfide or carbamate linkages, using covalent coupling methods known in the art. In another embodiment of the invention, where the targeting moiety T is an antibody, antibody fragment or peptidic sequence the fluorochrome is preferably conjugated via the free amino groups of the targeting moiety T via an amide bond.

Another aspect of the invention provides for the in-vitro use of the fluorescent conjugates comprising a fluorochrome moiety F coupled to a targeting moiety T having affinity to a tumour marker, wherein moiety F has the formula (I) or (II), or for the in-vitro use of a composition comprising said fluorescent conjugates, for the detection of a tumour cell in a sample, or for diagnosing and/or monitoring a tumour.

In particular, the fluorescent conjugates may be used for the detection of tumour cells and tumours expressing a tumour antigen such as CEA. In such cases, the targeting moiety T is preferably selected from a non-peptidic ligand, an antibody, an antibody fragment, and a fusion protein comprising at least one variable region of an antibody, such as defined in any of the previously described preferences and options. The fluorescent conjugate may be used for detection of a tumour cell or may be used for diagnosing or assisting the diagnosis of a cancer condition by in-vitro testing of a sample obtained from a patient from a body fluid such as blood serum, or from a tissue biopsy. Preferably, the tumour is a solid tissue tumour such as obtained or derived from the colon, rectum, stomach, intestine, bile duct, pancreas, oesophagus, ovary, breast, prostrate, liver or lung. Further, the fluorescent conjugates may be useful for monitoring for the presence or the progression of a tumour, for example for the assessment for any residual tumour cells or tumour tissue after resection surgery and/or chemotherapeutic treatment.

In a further aspect, the invention provides the use of the conjugate and/or the composition comprising the conjugate as described herein as a medicine. As used herein, a medicine means a material or product that is administered for any medical purpose, such as for diagnosis or treatment, including prophylactic treatment, of a disease or condition of a human subject or of an animal. In particular, the invention provides the use of the conjugate and/or the composition comprising the conjugate as described herein as a diagnostic medicine or agent. The use comprises the single or repeated administration of the conjugate, or the composition, to the subject in need thereof. In one embodiment, the subject in need of the conjugate or composition is a subject that has developed a cancer, or is at risk of developing a cancer.

The invention moreover provides for the use of the fluorescent conjugate and/or composition thereof in the detection of foci of a tumour that expresses the tumour marker or for determining the location of a tumour that expresses the tumour marker in a patient. The use may be particularly advantageous in patients affected by a cancer characterised by a disease progression such as recurrence, metastases or seeding. Such cancer progressions can result in a wider distribution of tumour cells or tissue masses. In particular, the fluorescent conjugate or the composition may be used for the detection of foci or for determining the location of a tumour which expresses the tumour marker or tumour antigen, i.e. the tumour marker to which moiety T has affinity, preferably at the cellular surface. As understood herein, the term foci means the group or clusters of cells or tissue defining a tumour or a lesion which may develop into a tumour and distinguishing it from the surrounding normal tissue.

In a preferred embodiment, the tumour expresses CEA. In another preferred embodiment, the patient has colorectal or gastrointestinal cancer. In advanced manifestation of such cancers, the patient may have peritoneal carcinomatosis, in which widespread metastases of cancerous tumours occur on the lining of the peritoneal cavity. In a particular embodiment of the invention, the fluorescent conjugate comprising a fluorochrome moiety of formula (I) or (II) and a targeting moiety T which is a chimeric monoclonal antibody is used for the detection of foci of a tumour expressing CEA or for determining the location of a tumour expressing CEA in a patient.

During surgical resection of tumour tissue, the surgeon relies on visual appearance and palpation to discriminate between tumour tissue and normal tissue. Surgical resection is the surgical removal of, either completely or partially, tumour tissue present in tissue, structure or organ of a patient. Cancerous and malignant tumour tissue may often be present in small (for instance, sub-millimeter sized) nodules or lesions that are non-visible to the naked eye. Complete tumour resection is often critical for the prognosis of a patient and as such, it is important that a surgeon is able to correctly identify, distinguish the boundaries and margins of malignant tumour tissue from that of healthy tissue and resect said tumour tissues, as well as avoid the unnecessary removal or damage to healthy tissue or structures during surgical removal of the tumour and/or cytoreductive surgical treatment of a patient.

The fluorescent conjugate as described above and/or the composition comprising such conjugate have been found to be particularly useful in the detection of tumour cells or tumour tissue at a resection margin in a patient undergoing, or having undergone, resection surgery of a tumour that expresses the tumour marker. As understood herein, the term resection margin refers to a margin or rim of tissue surrounding tumour tissue. The margin of tissue surrounding the resected tumour should normally be non-cancerous tissue that is resected along with the tumour to ensure sufficient removal of all malignant tumour tissue, however as described above it may be difficult to determine the extent of the margin and/or the extent of tumour versus normal tissue. Optionally, the resection margin may also be understood as the intended resection margin, which may be determined or modified based on the use of the method of the invention.

The method of detecting tumour cells or tumour tissue at or near a resection margin in a patient undergoing or having undergone resection surgery of a tumour expressing a tumour marker, preferably wherein the tumour marker is a tumour antigen, using the fluorescent conjugate of the invention or composition thereof is useful for assisting surgeons during and after surgery, e.g. cytoreductive surgery, so as to ensure that all tumour tissue is removed and that clean (or negative) margins, i.e. margins in which no tumour cells are detected may be obtained. In a preferred embodiment, the resection surgery is of a tumour that expresses or overexpresses CEA.

The fluorescent conjugate or composition of the invention and as described in any of the preceding paragraphs may be used for the detection of tumour cells or tumour tissue, such as the detection of the foci of a tumour and/or determination of their location(s), as well as at a resection margin of a tumour from a patient during or after surgical resection of a patient, wherein the patient has colorectal, gastric, biliary, pancreatic, oesophageal, ovarian, breast, prostrate, liver or lung cancer. The tumour cell or tissue to be detected or located may be a form of carcinoma or sarcoma that expresses CEA. Preferably, the fluorescent conjugates are used for the detection of tumour nodules or lesions in the submilimeter size range, for example, in patients suffering from peritoneal carcinomatosis.

In a particular embodiment of the use of the fluorescent conjugate or composition of the invention for detecting or for locating tumour cell or tumour tissue or for detecting resection margins of a tumour during or after resection surgery, the tumour is a malignant gastrointestinal tumour and the fluorescent conjugate comprises a fluorochrome moiety F of formula (I), or preferably of formula (II) coupled to a targeting moiety T which is a chimeric monoclonal antibody directed against the GOLD-2 epitope of CEA, comprising heavy chains of the G1m3 allotype and light chains of the km3 allotype, each heavy chain and each light chain comprising at least one mouse IgG1 variable domain and at least one human constant domain. The gastrointestinal tumour may refer to a tumour located in any part of the gastrointestinal tract, for example in the oesophagus, stomach, small intestine, large intestine, rectum, as well as organs associated with digestion such as the pancreas, liver and gallbladder, and may be in the submilimeter size range. Particularly preferred for such use are conjugates in which said chimeric monoclonal antibody comprises a variable light chain region of SEQ ID NO: 4 and a variable heavy chain of SEQ ID NO: 3.

In another particular embodiment of the use of the fluorescent conjugates of the invention for detecting or for locating tumour cell or tumour tissue or for detecting resection margins of a tumour during or after resection surgery, the tumour is a (malignant) breast tumour and the fluorescent conjugate used comprises a fluorochrome moiety F of formula (I), or preferably of formula (II) coupled to a targeting moiety T which is a chimeric monoclonal antibody directed against the GOLD-2 epitope of CEA, comprising heavy chains of the G1m3 allotype and light chains of the km3 allotype, each heavy chain and each light chain comprising at least one mouse IgG1 variable domain and at least one human constant domain. Particularly preferred for such use are conjugates in which said chimeric monoclonal antibody comprises a variable light chain region of SEQ ID NO: 4 and a variable heavy chain of SEQ ID NO: 3. Breast tumour as used herein may refer to a tumour located in any tissue associated with the breast or mammary tissue, including gland or ductal tissue and may also include regional lymph nodes, such as found in the axilla. Such tumours may be in the submilimeter size range.

In a further aspect, the use of the fluorescent conjugates or compositions of the invention such as for the detection of foci of tumours and determination of their location or for the detection of tumour cells or tumour tissue at a resection margin in a patient undergoing or having undergone resection surgery of a tumour comprises the steps of:

(a) administering the conjugate or composition to a patient suffering from a tumour;

(b) commencing tumour resection surgery on said patient;

(c) illuminating a tissue at a resection site of the patient undergoing the resection surgery with light having a wavelength of about 660 to 700 nm, wherein step (b) is performed within a period of not more than about 96 hours or 72 hours after step (a).

All uses of the conjugate or composition described herein may also be expressed, alternatively, as methods, in particular method for diagnosing or treating a patient. For example, the use in detecting foci of a tumour that expresses the tumour marker or for determining the location of a tumour that expresses the tumour marker in a patient may also be understood as a method of detecting foci of a tumour that expresses the tumour marker or of determining the location of a tumour that expresses the tumour marker in a patient.

As a further alternative, all diagnostic and/or therapeutic uses of the conjugate or composition described herein may also be expressed as uses of the conjugate or composition in the manufacture of a medicine or diagnostic agent (useful) for the specified diagnostic and/or therapeutic uses.

In step (a) of the method of treatment of patients for suffering from a tumour, the fluorescent conjugates or compositions thereof may be administered by injection or perfusion methods known in the art. In particular, the conjugates or compositions may be administered by intravenous, intraperitoneal, subcutaneous or intramuscular injection or perfusion. Alternatively, the fluorescent conjugates or compositions thereof may be administered by inhalation or topically. In this context, topic administration includes the direct administration to the skin or to an external or internal mucous membrane. Inhalation may be useful for the treatment of patients suffering from a tumour in their respiratory system, for example in the lung. When administered topically, the fluorescent conjugates or compositions thereof are preferably administered in the form of a spray.

The conjugate is preferably administered to the patient at a dose of 0.1 to 50 mg, or at a dose of 5 mg to 100 mg. In this context, dose means the amount of the conjugate and—if present—of the unconjugated antibody which is administered prior to e.g. a surgical or diagnostic procedure. The dose may optionally be divided and given at intervals. In the case of administration by injection to a patient having colorectal, gastric, biliary, pancreatic, oesophageal, ovarian, breast, prostrate, liver or lung cancer and undergoing resection surgery, the dose is preferably in the range from about 0.2 to 15 mg, such as from 0.5 to 10 mg or from 5 to 15 mg. Preferably, the administered dose is at least 5 mg. These dose ranges particularly apply to the conjugates and compositions having the preferred degrees of substitution as described above.

Preferably, step (b) is performed within a period of not more than about 96 hours after step (a). In other embodiments, step (b) is performed within a period of not more than 72 hours, or not more than 48 hours, or not more than 36 hours, or not more than 24 hours, or not more than 12 hours after completion of step (a).

In step (c) of the method, tissue at the resection site of the patient undergoing resection surgery is illuminated at a wavelength within the near infrared region. Optical devices for illumination used in step (c) preferably target the excitation wavelength of the fluorescent conjugates, preferably at a wavelength of between 660 to 700 nm. In an embodiment of the method, step (c) is performed by illuminating the tissue at a resection site of the patient undergoing resection surgery at an excitation wavelength of 680 nm.

In a particularly preferred embodiment of the method in treating a patient suffering from a tumour, the tumour is a malignant gastrointestinal tumour, and the fluorescent conjugate comprises a fluorochrome moiety F of formula (I), or preferably of formula (II) coupled to a targeting moiety T which is a chimeric monoclonal antibody directed against the GOLD-2 epitope of CEA, comprising heavy chains of the G1m3 allotype and light chains of the km3 allotype, each heavy chain and each light chain comprising at least one mouse IgG1 variable domain and at least one human constant domain.

In yet a further aspect of the invention, the fluorescent conjugate as featured in any of the above embodiments may also comprise or incorporate a radioactive isotope, a radiolabel or a radioactive tracer. The radiolabelled fluorescent conjugate may, for example, be obtained by direct radiolabelling of the conjugate, or by application of the radiolabel to the targeting moiety T prior to conjugation. The radiolabelled fluorescent conjugates, and compositions thereof, may be used as medicines in therapeutic and/or diagnostic applications. In one embodiment, the subject to which the radiolabelled conjugate or composition thereof is administered is a subject that has developed a cancer, or is at risk of developing a cancer.

EXAMPLES

Example 1—Preparation of Anti-CEA Chimeric Monoclonal Antibody

Gene Design and Synthesis

The nucleotide sequences (A) and (B) below, encoding for the native murine $V_H$ and $V_L$ variable domains respectively, were obtained from a murine anti-CEA antibody hybridoma, and are synthesized de novo and cloned into host pVVS Tandem expression vectors. These sequences incorporate a number of nucleotide modifications (without changing the native protein sequence) to ensure optimized cloning and optimized expression in CHO cells. KpnI and NheI restriction sites are inserted respectively at the 5' and 3' ends of the sequence coding for the $V_H$ domain. Similarly, two restriction site sequences, SalI and BSiWI were inserted respectively at the 5' and 3' end of the sequence coding for the $V_L$ domain.

(A) Heavy Chain (SEQ ID NO: 1):
GGTACCGCCGCCACCATGGACTCCAGACTGAACCTGGTGTTCCTGGTGCT

GATCCTGAAGGGCGTGCAGTGCGACGTGCAGCTGGTGGAATCTGGCGGAG

GACTGGTGCAGCCTGGCGGCTCCAGAAAGCTGTCTTGTGCCGCCTCCGGC

TTCACCTTCTCCAACTTCGGCATGCACTGGATCCGGCAGGCCCCTGAGAA

GGGCCTGGAATGGGTGGCCTATATCTCCGGCGGCTCCTCCACCATCTACT

-continued

TCGCCGACACCCTGAAGGGACGGTTCACCATCTCCCGGGACAACCCCAAG

AACACCCTGTTTCTGCAGATGACCTCCCTGCGGAGCGAGGACACCGCCAT

CTACTACTGCGCCAGAGACTACTACATCAACAACTACTGGTACTTCGACG

TGTGGGGCGCTGGCACCACCGTGACAGTGTCATCTGCTAGC

(B) Light Chain (SEQ ID NO: 2):
GTCGACGCCGCCACCATGGAATTTCAGACCCAGGTGTTCGTGTTCGTGCT

GCTGTGGCTGTCTGGCGTGGACGGCGACATCGTGATGACCCAGTCCCAGA

AATTCATGTCCACCTCCGTGGGCGACCGGGTGTCCATCACATGCAAGGCC

TCTCAGAACGTGCGGAGCGCCGTGGCCTGGTATCAGCAGACACCTGGCCA

GAGCCCCAAGGCCCTGATCTACCTGGCCTCCAACAGATACACCGGCGTGC

CCGATCGGTTCACCGGCTCTGGCTCTGGCACCGACTTCACCCTGACCATC

TCCAACGTGCAGTCCGAGGACCTGGCCGACTACTTCTGTCTGCAACACTG

GAACTACCCCCTGACCTTCGGCGGAGGCACCAAGCTGGAACTGAAGCGTA

CG

Vector Synthesis

The pVVS Tandem vector that was selected to serve as the host vector for Vu and $V_L$ genes was prepared by sequential double digestions using SalI/BsiWI and KpnI/NheI. This expression vector encodes the sequences of the constant domains of human IgG1 allotype G1m3 for the heavy chain and human IgG1 allotype Km3. The vector further comprises the following functional elements: a pCMV promotor (for both the heavy and light chains), a chimeric intron between the promoter and the initiation codon for translation, pUC replication origin, a BGH polyadenylation site, HS4 TK polyA insulator, a SV40 promoter and kanamycin/neomycin resistance genes for cell selection during vector amplification and after transfection. After digestion, the resulting vector backbone fragments were recovered using gel purification.

The insert fragments comprising the synthetic $V_H$ and $V_L$ gene inserts encoding for the native murine $V_H$ and $V_L$ domains as described above are extracted from their respective PVVS tandem expression vectors using KpnI/NheI and SalI/BsiWI respectively and recovered by gel purification.

All recovered fragments were pooled together and ligated to generate the final vector for transfection.

Transfection/Selection

The CHO cells transfected by the vector described above derive from the CHO (protein free) cell line (reference #00102307, lot 02K/008) obtained from the European Collection of Cell Cultures (ECACC). This cell line, originally acquired by ECACC in 1985, is a subclone of the parental CHO cell line derived from hamster ovary tissue and initially established by Puck et al. (1958).

The bank derived from the ECACC vial was named Bk1998. Cells were adapted to grow without Fetal Bovine Serum, then cloned by limiting dilutions. Subclone PF 3B9 was selected on the basis of growth properties and transfection capacity and banked (cell bank Bk4164). Cell bank BK4164, used to generate the cell substrate for antibody production of the antibody, was prepared from a vial of Bk21146.

CHO cells obtained from subclone 3B9 originally were thawed in EX-CELL® ACF CHO medium supplemented with 4 mM L-glutamine and grown at 37° C. in a 5% $CO_2$ humidified atmosphere under orbital shaking. Transfection was performed 2 days after the fifth passage. The expression vector as prepared above was linearized by digestion with SWaI restriction enzyme. Transfection was performed in triplicate by Nucleofection™ (Amaxa) with 10 µg DNA and incubated at 37° C., 5% $CO_2$ without shaking for 3 days. After a 3-day recovery period, selection was initiated by the addition of geneticin (0.5 g/L). Cells submitted to the Nucleofection™ conditions without DNA were used as a control of antibiotic selection.

Limited dilution cloning was performed after cell viability reached at least 80% under geneticin selection pressure. For each of the 3 transfection pools, forty 96-well plates were seeded at a target cell density of 0.5 cells/well. From these pools, 475 clones derived from a single cell were generated. After approximately 18 days of culture, antibody concentration was evaluated by ELISA to select 150 best-producing clones for scale up in 24-well plates. After the cells reached sufficient density, these were transferred to 6 well plates. Further selection was performed based on 10-day batch kinetics and mAb production as assessed by FastELISA for shake-flask scale up. Further selection based on fed-batch kinetics and mAb production as assessed by protein A HPLC (scale up to 2 L bioreactors) resulted in the selection of a lead clone for antibody production.

Antibody Production

Cells from the lead clone are thawed and transferred to revitalization medium (EX-CELL® ACF CHO medium, 4 mM L-glutamine) Viable cell density is determined and after centrifugation the cell pellet is resuspended in the medium to a density of $2 \times 10^6$ cells/mL after seeding in a 75 cm$^2$ flask. Cells are grown at 37° C.±1° C., 8%±2% $CO_2$ under orbital shaking. From day 2, the culture is scaled up in shake flasks of increasing capacity in EX-CELL® ACF CHO medium, 4 mM L-glutamine at 37° C.±1° C., 8%±2% $CO_2$ under orbital shaking. Cell viability, density and growth are assessed at each passage and absence of contaminants is checked via microscopic inspection. On day 17, after 7 passages, the contents of the shake flasks are pooled. The cells are counted and used to seed two 15-L bioreactors at a density of $0.5 \times 10^6$ viable cells/mL in a volume of 7 L. The cells are grown in fed-batch culture in EX-CELL® ACF CHO medium, 5 mM L-glutamine, 0.2% pluronic at 37° C. with pH and oxygen regulation for 20 days. BalanCD™ CHO Feed 3, glucose and L-glutamine are added as needed. Cell density, viability, pH are evaluated daily; samples are also taken daily from day 6 to determine glucose concentration and from day 10 to assess antibody concentration (protein A HPLC).

Clarification is performed on day 20 by passing the cell suspension from each bioreactor through three depth filters in parallel and then directly through a 0.2 µm filter. The clarified bulk harvest is collected and tested for antibody content by protein A HPLC, recombinant protein identity by Western blot analysis, bioburden, mycoplasma and spiroplasma contamination. The bulk harvest is distributed in 2 L PET bottles and stored at −70° C. to −90° C.

Further processing of the bulk harvest is performed as follows: The clarified bulk harvest is thawed for 24 h at 15-25° C., and the contents of various bottles are pooled and homogenized by magnetic stirring. The pooled bulk harvest is first purified on a protein A affinity chromatography column equilibrated with a 50 mM sodium phosphate, 300 mM NaCl, pH 7.0 buffer. After washes with the equilibration buffer and then with a 25 mM sodium phosphate, pH 7.0 buffer, the antibody is eluted using a 25 mM sodium acetate pH 3.5 buffer. The antibody peak (based on eluant absorbance at 280 nm) is collected and the antibody eluate is kept at 15-25° C. prior to pH adjustment step.

The pH of the antibody eluate is adjusted to pH 3.8 using 0.2M citric acid and incubated for 60-65 min at 15-25° C. whilst stirring. After neutralization to pH 6.5 with 0.5 M Na$_2$HPO$_4$, the solution is filtered on a 0.2 µm filter, collected and stored at 2-8° C.

The pH-inactivated antibody solution is further purified by cation exchange chromatography using a sulfonate ligand resin. The pH of the solution is adjusted to 5.0 using 0.2 M citric acid and loaded on a column previously equilibrated with 25 mM sodium acetate, pH 5.0 buffer. After washes with the equilibration buffer, the antibody is eluted with 25 mM sodium acetate, 195.2 mM NaCl, pH 5.0 buffer. Collection is based on absorbance at 280 nm.

The resulting antibody solution is further purified by anion exchange chromatography using quaternary ammonium ion exchange membranes equilibrated in 24 mM sodium phosphate, 53.4 mM NaCl, pH 7.0 buffer. The pH of the cation exchange chromatography eluate is adjusted to pH 7.0 using 0.5 M Na$_2$HPO$_4$ and diluted with a 25 mM sodium phosphate, pH 7.0 buffer to reach a final conductivity of 11 mS/cm. The solution is loaded on the membranes and the antibody is collected in the flow-through based on absorbance at 280 nm. The collected solution is filtered on a 0.2 µm filter into a sterile, single-use PET container and stored at 2-8° C.

The antibody solution is then concentrated by ultrafiltration and diafiltered against a 10 mM Tris-HCl, pH 7.2 buffer using 30 kDA cut-off membranes. The retentate of the filtration is collected and stored at 15-25° C.

The retentate is then diluted to 1 mg/mL with a 10 mM Tris-HCl pH 7.2 buffer and passed through a 0.2 µm filter, followed by nanofiltration (Planova 15 N membrane) previously equilibrated with the same buffer. The filtrate is stored at stored at 15-25° C. In a final step, the resulting purified bulk antibody solution is filtered through a 0.2 µm filter, distributed into sterile PET bottles and stored at −70 to 90° C.

Samples are taken for antibody concentration determination by protein A HPLC during each of the purification steps.

The resulting antibody product was characterized by methods known in the art such as UPLC-UV-MS. The molecular weight of the antibody is 148.6 kDA as determined by MALDI-TOF mass spectrometry.

Example 2—Preparation of Fluorochrome of Formula (IV)

Acetanilide Intermediate (B):

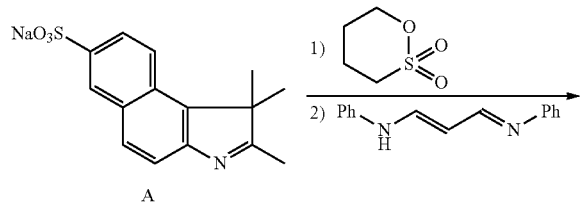

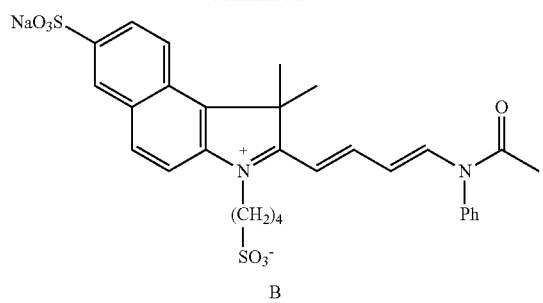

Sulfonated indolenine A is reacted with 1,4-butane sultone. The resulting intermediate is reacted with beta-anilino-acrolein to provide the acetanilide intermediate B.

Intermediate Compound (D):

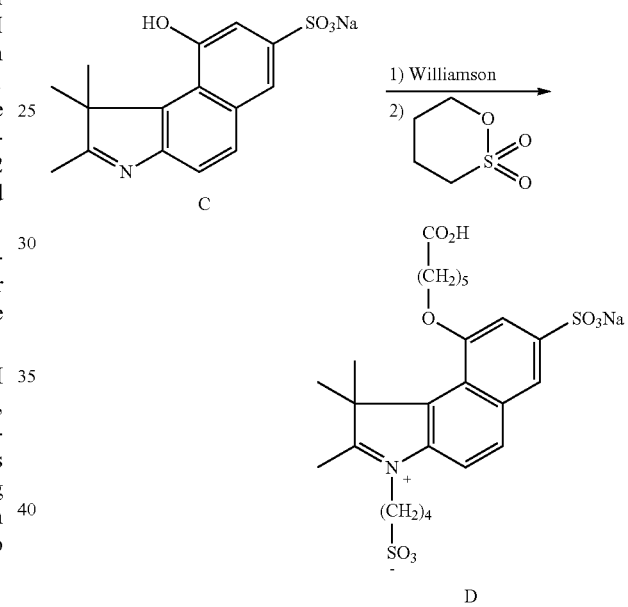

Intermediate D is prepared via Williamson condensation to form a carboxyalkyloxy derivative of the indolenine precursor C followed by quaternization with 1,4-butane sultone. Indolenine C is obtained by diazotation/reduction of an aminated aromatic precursor followed by sulfonate formation, hydroxylation and Fischer cyclization with ketone.

Fluorochrome of Formula (IV):

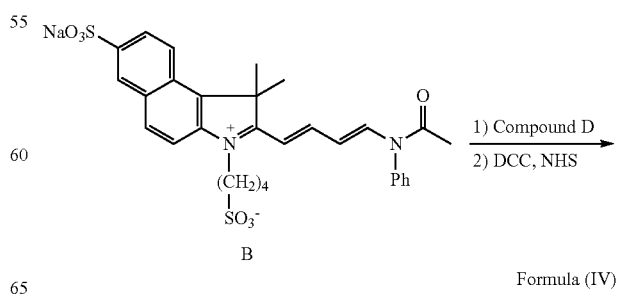

Formula (IV)

Compound B is condensed with indole compound D. The resulting dicarbocyanine compound was activated with N-hydroxysuccinimide (NHS) to provide the fluorochrome of Formula (IV).

Example 3—Conjugation of Fluorochrome to the Anti-CEA Chimeric mAb

The purified antibody of Example 1 is thawed for approximately 24 hours at 15-25° C. Ultrafiltration/diafiltration with 30 kDa cut-off membranes to perform a buffer exchange (0.1 M sodium phosphate/carbonate, pH 9.3). The fluorochrome (Formula (IV) of Example 2) is dissolved in DMF at a concentration of 2.25 mg/mL by overnight stirring at 15-25° C. DMF is added to the solution of the antibody (diluted to a final concentration of 1 mg/mL using 0.1 M sodium phosphate/carbonate buffer, pH 9.3) to a final concentration of 10% v/v. The solution of fluorochrome is then added to the antibody solution at a flow rate of 20 mL/min at a molar excess of 4.5. The resulting reaction mixture is incubated under orbital shaking at ambient temperature for ca. 45 min.

A second ultrafiltration/diafiltration step is performed (30 kDa cut-off membranes) first with PBS-135 mM L-Arginine supplemented with 10% (v/v) DMF, followed by the formulation buffer PBS-135 mM-L-arginine to remove the DMF. The retentate is then diluted to a final concentration (as determined by spectrophotometric analysis) of 1.0-1.1 mg/mL using the formulation buffer and filtered (0.2 μm).

The resulting fluorescent conjugate is filled into 0.5 L PET bottles closed with high density polyethylene caps, inserted into amber plastic bags and stored at −20° C.±5° C.

Fluorochrome/antibody molar ratio is determined by spectrophotometry. An average conjugation ratio of 1.5-1.6 is observed.

Conjugation of the fluorochrome to the antibody may alternatively be performed with DMSO as the conjugation solvent. Addition of the fluorochrome at a molar excess of 4 to the antibody (at a solution concentration of 1 mg/mL), with a final reaction concentration of 10% v/v of DMSO, and a reaction time of between 5 to 120 min provided a conjugate with an average conjugation ratio of between 1.5-1.6, as determined by spectrophotometry. No significant difference was observed in respect of fluorescence emission intensity, photobleaching, and quantum yield measurements obtained for these fluorescent conjugates prepared in DMSO in comparison to conjugates prepared under analogous concentrations and conditions in DMF.

Example 4—Formulation

The buffer used for formulation of the fluorescent conjugate as prepared according to Example 3 may be adapted as needed for the uses and methods within the context of the invention. For example, the fluorescent conjugate may be preferably formulated in a buffer comprising 10 mM $KH_2PO_4$ (VWR Prolabo) 10 mM Na3Citrate/Citric acid (Fluka), 300 mM Arginine HCl (Sigma), 0.02% (w/v) Tween 20 (Merck), wherein the pH is adjusted to 6.0.

Example 5—Conjugate Characterisation

Fluorescence Studies

The quenching, photobleaching and fluorescent quantum yield of the fluorochrome of Formula (IV) and of a fluorescent conjugate as prepared according to Example 3 were determined at the excitation wavelength of 680 nm (provided with the optical device Fluobeam700), the wavelength relevant for clinical use.

Samples of the fluorochrome of Formula (IV) in DMF and samples of the fluorescent conjugate of Example 3 in PBS 135 mM-Arginine were prepared at various concentrations ranging from 0.05-500 μM.

Maximal fluorescence intensity and maximal concentration of fluorochrome before the detection of quenching i.e. the auto-inhibition of the emitted fluorescence by the fluorochrome itself at a certain concentration) were determined using a fluorimeter.

The fluorescence values were obtained after subtraction of the background fluorescence values of the buffers. For the fluorescent conjugate the maximal fluorescent intensity was measured to be 70 AU (arbitrary units), with a maximal concentration of 5 μM before quenching is observed. For the fluorochrome, maximal fluorescent intensity was measured to be 120 AU and at a maximal concentration of 10 μM.

The quantum yield as a measure for the efficiency of the conversion of absorbed light into emitted light was calculated for the samples at a concentration of 5 μM at the clinical wavelength of 680 nm. For the unconjugated fluorochrome of Formula (IV), a quantum yield of 0.26 was determined, whereas for the conjugated fluorochrome a quantum yield of 0.15 was observed, amounting to a decrease of only 43%.

In terms of clinical use, in particularly during tumour resection surgeries, the fluorochrome of the fluorescent conjugate should maintain a stable and adequate level of fluorescence intensity for as long a period of time as possible.

Photobleaching, or loss of fluorescent activity was also evaluated at the clinical excitation wavelength of 680 nm for samples of the fluorochrome and the conjugate, as well as a commercially available carbocyanine fluorochrome, Alexa Fluor® 680, which is a far red emitting dye that has maximal absorption and emission wavelengths similar (maximal absorption of 679 nm and maximal emission at 702 nm) to that of the fluorochrome of Formula (IV). Photobleaching was also evaluated for a conjugate prepared in analogy to the conjugation method described in Example 3 of the anti-CEA chimeric mAB of Example 1 and Alexa Fluor® 680 (an average fluorochrome to antibody ratio of about 1.46 was obtained). Samples of these conjugates was prepared in PBS 1×.

The samples were prepared at concentrations of 5 μM and exposed to light at 680 nm. Emitted fluorescence intensity was measured at intervals of 0 h, 30 min and 1, 1.5 and 2 h of light exposure.

TABLE 1

Fluorescence emission over time ($\lambda_{ex}$ = 680 nm)

| | Exposure Time (h) | | | | |
| --- | --- | --- | --- | --- | --- |
| | 0 | 0.5 | 1 | 1.5 | 2 |
| Fluorochrome (Formula IV) | 100.00 | 79.73 | 83.29 | 73.74 | 66.3 |
| Conjugate of Example 3 | 100.00 | 69.59 | 35.75 | 25.43 | 15.14 |
| Alexa-Fluor 680 | 100.00 | 52.13 | 16.22 | 5.74 | 2.01 |
| Alexa-Fluor 680 Conjugate | 100.00 | 9.04 | 2.27 | 0.98 | 0.62 |

After 30 minutes of continuous exposure at the clinical wavelength of 680 nm, the fluorescence of the fluorescent conjugate is around 70%, whereas the emitted fluorescence of the commercial dye conjugated to the same antibody is only about 9%. After 1 hour, the fluorescence intensity of the commercial dye as well as its conjugate is almost nil, whereas fluorescence of the fluorescent conjugate and unconjugated fluorochrome is still maintained.

Tissue Cross-Reactivity

A tissue cross-reactivity study of the fluorescent conjugate prepared as in Example 3 using biotin labelled conjugate was carried out on a panel of 42 human frozen tissues and blood smears from three unrelated individuals using standard immunohistochemical techniques. Specific staining of the antibody conjugate was found to be limited to the digestive tract and a few other tissues, in epithelial components, primarily on the apical cell border or luminal side, that have been described in the literature to express CEA, confirming on-target only binding of the antibody.

Antigen Affinity

The affinity of the fluorescent conjugate as prepared in Example 3 to the target carcinoembryonic antigen was also determined, using surface plasmon resonance (SPR) on a BIACORE 3000 device. Carcinoembryonic antigen was coupled to a CM5 chip via the thiol groups (Surface Thiol Coupling GE healthcare; Instruction 22-0618-10AB). Association and dissociation rates were measured using in the flow 6 different concentrations (from 50 nM to 1.5 nM) of the chimeric monoclonal antibody of Example 1, the monoclonal antibody m511 (the original murine antibody from which the variable regions the chimeric monoclonal antibody of Ex. 1 is based) and fluorescent conjugate. Data acquisition and parameters calculations were performed using the Bia software and Bia evaluation programs. The affinity of chimeric monoclonal antibody of Example 1 to CEA ($3.27\times10-11$ nM) remained very close to that of the parental murine 511 antibody ($3.82\times10-11$ nM) and was not modified following its labelling with the near-infrared fluorochrome dye of (KD of the fluorescent conjugate of Ex. 3 was measured as $3.21\times10-11$ nM).

Example 6—In Vivo Studies

The efficacy of the fluorescent conjugate of Example 3 was assessed in vivo in four different mouse models expressing human CEA.

Tissue distribution of the fluorescent conjugate was assessed by radioactivity measurements using single-photon emission computed tomograph (SPECT) in a LS-174T peritoneal carcinomatosis mouse model which was set up according to established protocols. Immunosuppressed NMRI nude mice were subjected to LS-174T cell transplant via intraperitoneal injection with CEA-overexpressing LS-174T cells. The mice were intravenously injected 10 days later with 30 and 50 μg of $^{125}$I-radiolabelled fluorescent conjugate (which was prepared by incubation of the fluorescent conjugate with a radiolabel iodination reagent). Visualization of the mice 48 hours after treatment with 50 μg of the conjugate (conducted using a Nano-SPECT-CT (Bioscan®) camera) revealed that radioactivity was essentially limited to the tumor nodules present in the peritoneal cavity of the mice. This result corresponded with the biodistribution measurements of radioactivity in the different organs obtained after sacrifice of the animals.

In vivo fluorescence visualization studies was also conducted by injection of the non-radiolabelled fluorescent conjugate into immunosuppressed NMRI nude mice of LS-174T human tumor cells overexpressing CEA. After 12 days of development of carcinomatosis, the animals received 20 or 30 μg of the fluorescent conjugate intravenously. After 48 hours, the animals were sacrificed and fluorescence was visualized using an optimal probe at excitation and emission wavelengths of 680 nm and 700 nm respectively. At both doses, fluorescence distribution was clearly limited to the peritoneal tumours, allowing clear visualization of the micro-nodules in the peritoneal cavity, including the area of the pancreas (FIG. 1, Column A, in situ tumours visualized at 700 nm). Nodules of less than 1 mm, and weighing less than 1 mg (0.2-1.7 mg) were identifiable and fluorescent (FIG. 1, Column B demonstrating the individualized resected tumours of the same animals featured in Column A, visualized at 700 nm). Injection of the fluorescent conjugate into healthy animals and a non-relevant fluorescent conjugate (with a PX antibody i.e. IgG1 monoclonal antibody purified from mouse myeloma MOPC21 (ref Köhler et al, Eur J Immunol 1976 (6) 292)) as controls did not induce any specific staining.

Notably, the fluorescent conjugate allows for visualization of tumor nodules overexpressing CEA, irrespective of the location of the tumour nodules, thus mimicking clinical conditions.

A model based on an orthotopic mouse model of human colorectal cancer expressing human CEA (Tseng et al, Vis. Exp. 2007 (10) 484) was used. HT29 cells overexpressing CEA were injected subcutaneously at 4 sites on the back of six-week old CD1-FOxn1$^{nu}$ immunosuppressed female mice to induce subcutaneous human colon tumour development. Small tumour fragments (approx. 3 mm in diameter) were then removed and transplanted into the cecal wall of the animals to induce the development of orthotopic tumours. The cecal wall was slightly damaged to induce an immune reaction and to facilitate tumour cell infiltration. After development of these tumours, 30 μg of the fluorescent conjugate according to the invention (or of a fluorescent conjugate with a non-relevant PX antibody, as a control) was injected intravenously into the animal. Fluorescent signal in the near infrared (700 nm) was measured at 0, 4, 24 and 48 hours after injection using the PEARL imaging system (Li-Cor Biosciences) for the subcutaneous tumors or the FLARE intraoperative imaging system (Curadel) for the orthotopic tumours.

Figure 2A:
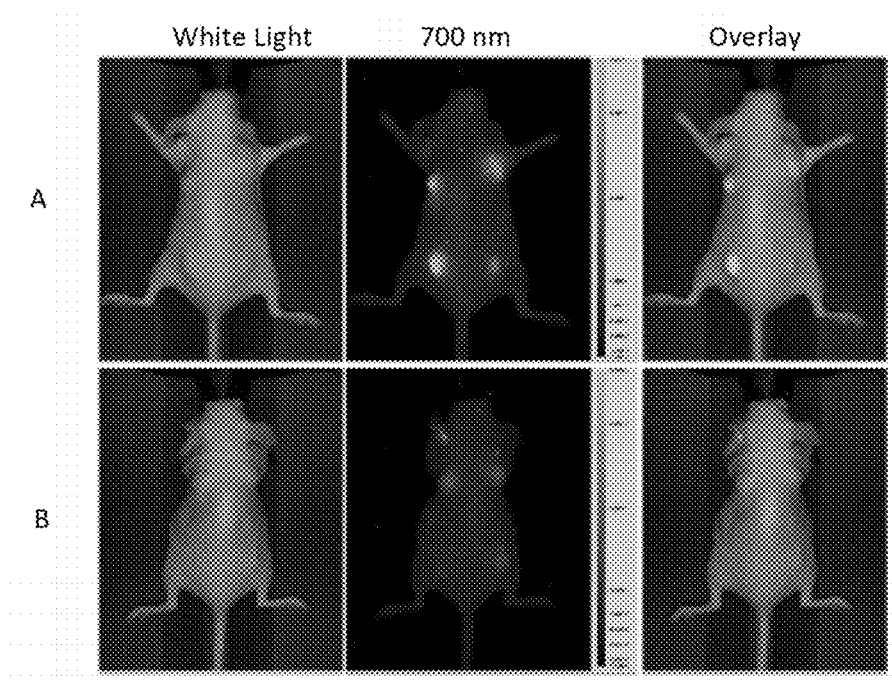
FIG. 2A depicts images of tumours in a subcutaneous tumour mouse model of human colorectal cancer (HT-29) overexpressing CEA, taken 48 hours after administration of 30 μg of the fluorescent conjugates (A—Ex. 3 fluorescent conjugate; B—control conjugate). The columns from left to right depict images taken in white light, fluorescence (visualization at 700 nm) and in overlay.
Figure 2B:
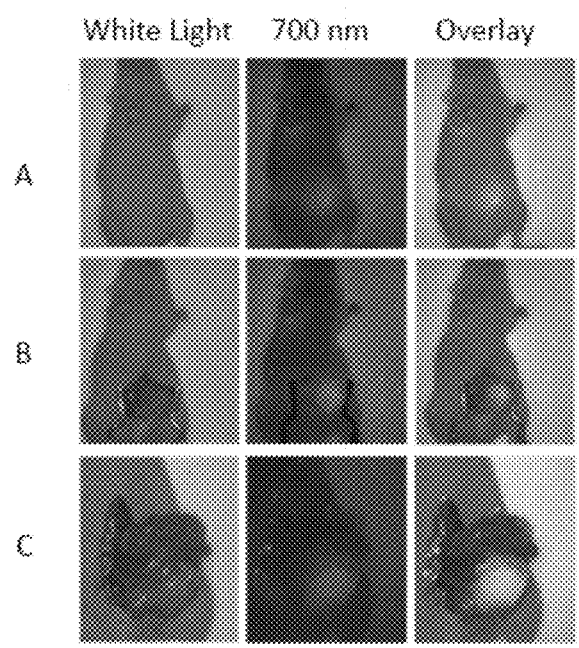
FIG. 2B depicts images of the tumours in an orthotopic tumour mouse model of human colorectal cancer (HT-29) overexpressing CEA, taken 48 hours after administration of 30 μg of the fluorescent conjugate of Ex. 3 (A—before incision, B—after incision, C—after exposure of the tumour). The columns from left to right depict images taken in white light, fluorescence (visualization at 700 nm) and in overlay.

In result, intraoperative immunophotodetection at 700 nm of the tumours at both subcutaneous and orthotopic locations was clearly observed (FIG. 2A and FIG. 2B respectively). The fluorescence of the subcutaneous tumours was of such high level that it was visible through the skin of the animals (FIG. 2A. Row A) 48 hours after injection of the antibodies.

Liver metastases of human tumours overexpressing CEA were also observed using the fluorescent conjugate of the invention. LS-174T cells or LoVo human colon adenocarcinoma cells were injected in the spleen of immunosuppressed Balb/c nude mice as described in published protocols (ref Tibbetts et al, Cancer 1993, (71), 315-21). Both cell types overexpress CEA and induce the development of liver metastases, but follow different patterns. LoVo cells induce the dissemination of many small metastases across the surface of the liver, whereas LS-174T cells induce the formation of only a few larger metastases. The mice subjects received 30 μg of the fluorescent conjugate 48 h before fluorescence visualization at 700 nm. As a control, mice were injected with a non-relevant conjugate based on PX antibody. It was found that tumour nodules of a very small size, e.g. micro-metastases on the surface of the liver, which were not detectable i.e. visible to the naked eye, could be detected under fluorescence in the mice injected with the fluorescent conjugate, which defined the outline of these tumours. Furthermore, it was established that visualization of the liver metastases is enabled regardless of cell line of the tumour modules. No detection of tumours was observed with the control.

A similar study was conducted with a model for pancreatic tumours. Six week-old athymic CD1-Foxn1$^{nu}$ immunosuppressed female mice were used in the study, and anaesthetized with isoflurane during tumour inoculation and imaging procedures. Orthotopic pancreatic tumours were obtained as described in Kim et al, Nat. Protoc., 2009, 4, 1670-80. The spleen and pancreas of the animals were both laterally externalized through a lateral excision to expose the pancreas' entire length. A fine needle was passed parallel to the vasculature into the pancreas through which 500 000 BXPC-3-luc2 cells (luciferase transfected cell line) were injected. Growth of the orthotopic tumours was monitored weekly by bioluminescence imaging (BLI), which was conducted by injection of 150 mg/kg of a D-luciferin solution (SynChem, Inc) in PBS intra-peritoneally in a total volume of 50 µL, 10 min prior to imaging using the IVIS spectrum imaging system (Perkin Elmer Life Sciences). Once the orthotopic tumors were detectable via BLI, 30 µg of the fluorescent conjugate was injected intravenously through the tail vein of the animals. The animals were sacrificed 48 hours after injection, and examined under near infrared at 700 nm. Clear visualization of the orthotopic pancreatic tumours was observed. No visualization was observed in control mice injected with non-specific conjugate or the fluorochrome dye alone.

Signal-to-background ratio was calculated using the NIR fluorescent signals measured using the Pearl Impulse small animal imaging system (LI-COR). The images were normalized and regions of interest were selected for analysis. The mean tumour specific signal was divided by the mean signal from the surrounding tissue to provide mean signal-to-noise ratios. A two-way repeated measurement ANOVA using the Bonferroni correction was used to assess significant signal-to-background ratios from different groups at all time points. In contrast to the free fluorochrome dye, or the non-relevant control conjugate, which had signal-to-background ratio values close to 1, the signal-to-background ratio for the fluorescent conjugate was greater than 3.

Immunohistochemical analysis of resections of the BXPC-3 subcutaneous tumours with hematoxylin-Eosin staining confirmed that the fluorescent conjugate was bound to the tumour, as opposed to the controls which only appeared as non-specific staining around the tumour cells.

In summary, it was found that the fluorescent conjugate such as prepared according to Example 3 allowed for the in vivo identification of tumour nodules overexpressing CEA, irrespective of the location of the tumours, and the origin (i.e. colorectal versus pancreatic) of the tumour, confirming the targeting ability of the fluorescent conjugate. A high level of signal of noise ratio was observed, allowing for the detection of very small nodules invisible to the naked eye.

Pharmacological studies to assess the safety and toxicity of intravenous administration of the fluorescent conjugate also demonstrated that there were no significant adverse effects on the central and peripheral nervous systems in Wistar rats, nor on the cardiovascular and respiratory functions in Beagle dogs, and that the conjugate is well tolerated up to maximal dose levels tested of up to 40 mg/kg per day in the rats (85-fold intended clinical dose) and 5 mg/kg (10-fold the intended clinical dose) in the dogs.

Example 7—Clinical Studies (a) Peritoneal Carcinomatosis—

A clinical study to assess safety and performance of a conjugate of Ex. 3 in 15 human patients with peritoneal carcinomatosis (metastatic tumours) of digestive origin.

Doses of the fluorescent conjugate of Example 3 in the range of 5 to 15 mg were administered by intravenous injection. Preliminary results show that no adverse reactions are observed at any of these doses.

(b) Colorectal and Pancreatic Cancers—

A clinical study to assess the safety and performance of the fluorescent antibody conjugate of Example 3 in 30 human patients with cancer of the rectum or pancreas.

A study using a 5-mg dose of the fluorescent conjugate injected intravenously 48 hours before surgery was conducted. In the patients studied thus far, no adverse effects were reported during or directly after dosing. In general, no clinically significant changes in vital signs from baseline values were observed.

Preliminary results demonstrate a very clear localization of fluorescence at suspected tumour sites. Intraoperative visualization was performed using an Artemis Open Imaging System (Quest Medical Imaging) configured to settings as appropriate for the fluorescent conjugate.

Figure 3:
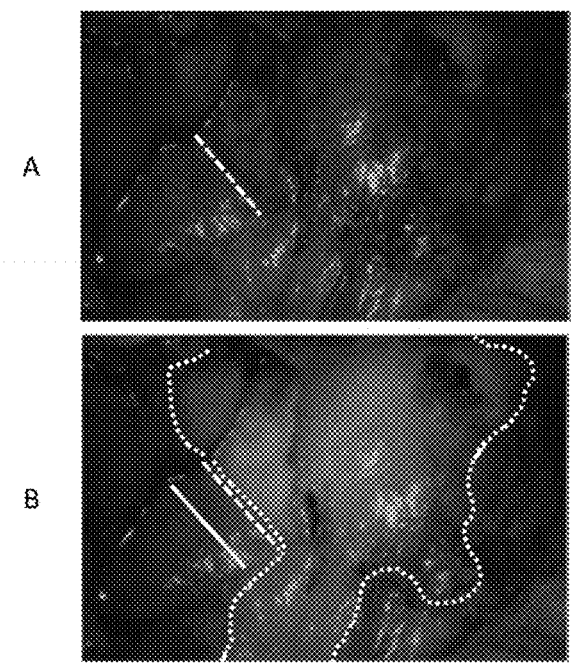
FIG. 3 depicts images taken during surgery of a primary pancreas tumour in a patient, 48 hours following administration of 5 mg of the fluorescent conjugate of Ex. 3 (A is under white light, and B is the image overlay with fluorescence). The dashed line represents the proposed resection margin based on visualization and palpation only, whereas the solid line presents the proposed resection margin based on fluorescence visualization. The dotted line represents an approximate outline of the tumour as shown by the fluorescence.
Figure 4:
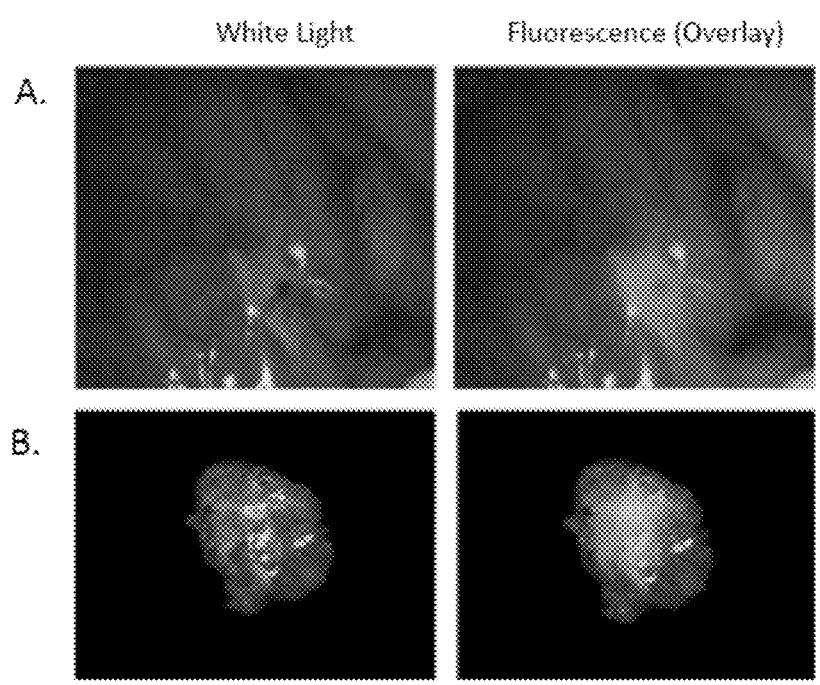
FIG. 4 depicts images of a peritoneal metastasis of a pancreatic cancer patient, 48 h after administration of 5 mg of the fluorescent conjugate of Ex. 3. The images in row A were obtained intraoperatively in vivo and the images in row B are ex vivo after resection (left column under white light, and right column with fluorescence as an overlay image).

In one pancreatic cancer patient, the use of the fluorescent conjugate led to the identification of tumour cells located in a region which would normally have been considered a tumour-free resection margin around the primary tumour localized in the body of the pancreas (i.e. leading to retention of the tumour tissue), based on visual inspection and palpation alone (FIG. 3—the proposed resection margin as determined by visual inspection and palpation alone is represented by the dashed line, which would have been too close to the tumour tissue, the bulk of which is represented by the dotted line. The proposed resection margin as determined by fluorescence is represented by the solid lines). Due to the presence of many peritoneal metastases, only exploration and staging was performed, i.e. only the metastases were resected for biopsy and further analysis on the back table in the operating room. The fluorescent conjugate provided clear demarcation of the foci as well as the margins of the metastases both in-vivo and ex-vivo in the excised tumour subsequent to resection (FIG. 3, row A: image of a metastasis in vivo under white light and under fluorescence (overlay image); FIG. 3, row B: image of the excised metastasis ex vivo under white light and under fluorescence (overlay image)).

Similar results were observed in another pancreatic cancer patient following administration of the fluorescent conjugate. Fluorescence clearly delineating the suspected tumour, which was located near the head of the pancreas was observed.

In a patient diagnosed with colorectal metastasis, a 5-mg dose of the fluorescent conjugate was administered 48 h prior to resection. The dose was well-tolerated with no adverse events observed. A clear fluorescence signal was detected at the lymph node para-iliacal left site suspected for the metastasis, delineating the metastasis. A successful resection was performed.

A patient with locally advanced rectum carcinoma was also administered a 5 mg dose of the fluorescent conjugate. The dose was well-tolerated with no adverse events detected. A laparoscopic low anterior resection was performed. The resected rectum tissue was visualized in the operating room back table. A clear delineation of the tumour tissue in the resected tissue was observed.

What is claimed is:

1. A fluorescent conjugate comprising a fluorochrome moiety F coupled to a targeting moiety T, wherein moiety F has the formula (I):

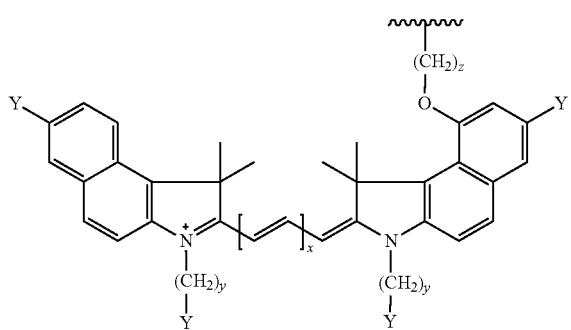

wherein

Y is independently for each occurrence selected from $SO_3H$, $SO_3-$, and $SO_3M$, wherein M is a monovalent cation;

x, z and y are independently selected from an integer of 1 to 8;

and wherein moiety T can bind or associate with a tumour marker, wherein the tumour marker is a tumour antigen.

2. The conjugate of claim 1, wherein Y is selected from $SO_3-$ and $SO_3Na$.

3. The conjugate of claim 2, wherein moiety F has the formula (II):

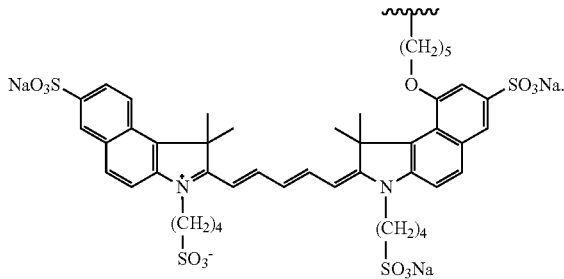

4. The conjugate of claim 1, wherein the tumour antigen is carcinoembryonic antigen (CEA).

5. The conjugate of claim 1, wherein moiety T is selected from an antibody, an antibody fragment, and a fusion protein comprising at least one variable region of an antibody; and wherein the antibody is optionally a chimeric monoclonal antibody (mAb).

6. The conjugate of claim 1, wherein the moiety T is a chimeric monoclonal antibody that binds to one or more epitopes of the CEA antigen.

7. The conjugate of claim 6, wherein moiety F has the formula (II), and wherein the chimeric monoclonal antibody is directed against the GOLD-2 epitope of CEA, comprises heavy chains of the G1m3 allotype and light chains of the km3 allotype, each heavy chain and each light chain comprising at least one mouse IgG1 variable domain and at least one human constant domain.

8. The conjugate of claim 7, wherein the chimeric monoclonal antibody comprises a variable light chain region of SEQ ID NO: 4 and a variable heavy chain of SEQ ID NO: 3.

9. The conjugate of claim 6, wherein there are multiple F moieties, nF, coupled to one T moiety, and wherein n is an integer selected from 1 to 4.

10. A composition comprising the conjugate of claim 1 in combination with one or more inactive ingredients comprising water for injection.

11. The composition of claim 10, wherein the average degree of conjugation of the conjugate in the composition is about 0.5 to 3.

12. The conjugate of claim 3, wherein the moiety T is a chimeric monoclonal antibody that binds to one or more epitopes of the CEA antigen.

13. The conjugate of claim 3, wherein the conjugate comprises nF moieties of Formula (II), coupled to one T moiety, wherein n is an integer selected from 1 to 4.

14. A composition according to claim 10, wherein the composition
    (a) is sterile and comprises an aqueous buffer and L-arginine, and/or
    (b) further comprises a compound comprising a T moiety which is not coupled to an F moiety.

* * * * *

SEQUENCE LISTING

<160> NUMBER OF SEQ ID NOS: 4

<210> SEQ ID NO 1
<211> LENGTH: 441
<212> TYPE: DNA
<213> ORGANISM: Artificial Sequence
<220> FEATURE:
<223> OTHER INFORMATION: Mus musculus with KpnI and NheI restriction
      sites

<400> SEQUENCE: 1

```
ggtaccgccg ccaccatgga ctccagactg aacctggtgt tcctggtgct gatcctgaag      60
ggcgtgcagt gcgacgtgca gctggtggaa tctggcggag gactggtgca gcctggcggc     120
tccagaaagc tgtcttgtgc cgcctccggc ttcaccttct ccaacttcgg catgcactgg     180
atccggcagg cccctgagaa gggcctggaa tgggtggcct atatctccgg cggctcctcc     240
accatctact cgccgacac cctgaaggga cggttcacca tctcccggga caaccccaag     300 aacacccctgt ttctgcagat gacctccctg cggagcgagg acaccgccat ctactactgc     360
gccagagact actacatcaa caactactgg tacttcgacg tgtggggcgc tggcaccacc     420
gtgacagtgt catctgctag c                                               441
```

<210> SEQ ID NO 2
<211> LENGTH: 402
<212> TYPE: DNA
<213> ORGANISM: Artificial Sequence
<220> FEATURE:
<223> OTHER INFORMATION: Mus musculus with SalI and BsiWI restriction
      sites

<400> SEQUENCE: 2

```
gtcgacgccg ccaccatgga atttcagacc caggtgttcg tgttcgtgct gctgtggctg      60
tctggcgtgg acggcgacat cgtgatgacc cagtcccaga attcatgtc cacctccgtg     120 ggcgaccggg tgtccatcac atgcaaggcc tctcagaacg tgcggagcgc cgtggcctgg     180
tatcagcaga cacctggcca gagccccaag gccctgatct acctggcctc caacagatac     240
accggcgtgc ccgatcggtt caccggctct ggctctggca ccgacttcac cctgaccatc     300
tccaacgtgc agtccgagga cctggccgac tacttctgtc tgcaacactg gaactacccc     360
ctgaccttcg gcggaggcac caagctggaa ctgaagcgta cg                        402
```

<210> SEQ ID NO 3
<211> LENGTH: 121
<212> TYPE: PRT
<213> ORGANISM: Mus musculus

<400> SEQUENCE: 3

```
Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asn Phe
            20                  25                  30

Gly Met His Trp Ile Arg Gln Ala Pro Glu Lys Gly Leu Glu Trp Val
        35                  40                  45

Ala Tyr Ile Ser Gly Gly Ser Ser Thr Ile Tyr Phe Ala Asp Thr Leu
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Ile Tyr Tyr Cys
                85                  90                  95
```

```
Ala Arg Asp Tyr Tyr Ile Asn Asn Tyr Trp Tyr Phe Asp Val Trp Gly
            100                 105                 110

Ala Gly Thr Thr Val Thr Val Ser Ser
            115             120

<210> SEQ ID NO 4
<211> LENGTH: 107
<212> TYPE: PRT
<213> ORGANISM: Mus musculus

<400> SEQUENCE: 4

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Ser Ala
            20                  25                  30

Val Ala Trp Tyr Gln Gln Thr Pro Gly Gln Ser Pro Lys Ala Leu Ile
        35                  40                  45

Tyr Leu Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
            85                  90                  95

Thr Phe Gly Gly Gly Thr Lys Leu Glu Leu Lys
            100                 105
```